United States Patent
Mikkaichi et al.

(10) Patent No.: US 7,735,489 B2
(45) Date of Patent: Jun. 15, 2010

(54) ENDOTRACHEAL TUBE, DEVICE FOR USE IN MEDICAL PROCEDURE THROUGH NATURAL OPENING AND MEDICAL PROCEDURE THROUGH NATURAL OPENING

(75) Inventors: Takayasu Mikkaichi, Tokyo (JP); Takahiro Kogasaka, Tokyo (JP); Tetsuya Yamamoto, Hanno (JP); Kensei Nakahashi, Tokyo (JP); Hironobu Kawano, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1081 days.

(21) Appl. No.: 11/331,977

(22) Filed: Jan. 13, 2006

(65) Prior Publication Data

US 2007/0163596 A1   Jul. 19, 2007

(51) Int. Cl.
*A61M 16/00* (2006.01)
*A62B 9/06* (2006.01)
(52) U.S. Cl. ............................. 128/207.14; 128/207.15
(58) Field of Classification Search ............ 128/207.14, 128/207.15, 200.26; 600/435, 466; 604/508, 604/96.01, 103.04, 43, 105, 106
See application file for complete search history.

(56) References Cited

U.S. PATENT DOCUMENTS

| 4,495,945 | A | * | 1/1985 | Liegner | 128/200.26 |
|---|---|---|---|---|---|
| 4,840,173 | A | | 6/1989 | Porter, III | |
| 5,067,497 | A | | 11/1991 | Greear et al. | |
| 5,151,086 | A | * | 9/1992 | Duh et al. | 604/506 |
| 5,458,131 | A | * | 10/1995 | Wilk | 600/105 |
| 5,536,250 | A | * | 7/1996 | Klein et al. | 604/103.01 |
| 5,620,408 | A | * | 4/1997 | Vennes et al. | 600/114 |
| 6,062,223 | A | * | 5/2000 | Palazzo et al. | 128/207.15 |
| 6,443,156 | B1 | * | 9/2002 | Niklason et al. | 128/207.14 |
| 2006/0032505 | A1 | * | 2/2006 | Alfery et al. | 128/207.14 |
| 2007/0017527 | A1 | * | 1/2007 | Totz | 128/207.15 |

* cited by examiner

*Primary Examiner*—Justine R Yu
*Assistant Examiner*—Colin Stuart
(74) *Attorney, Agent, or Firm*—Scully, Scott, Murphy & Presser, P.C.

(57) ABSTRACT

An endotracheal tube according to the present invention is used by being installed into a patient so as to use it together with a device having an insertion section which is inserted into the body. A portion overlapping with the device inserted into the patient is formed as a flat shape; and furthermore, an outer face portion formed along a longitudinal direction of a cross-section, of the portion formed in the flat shape contacts the device.

13 Claims, 11 Drawing Sheets

ENDOTRACHEAL TUBE, DEVICE FOR USE IN MEDICAL PROCEDURE THROUGH NATURAL OPENING AND MEDICAL PROCEDURE THROUGH NATURAL OPENING

BACKGROUND OF THE INVENTION

1. Field of the Invention

The present invention relates to an endotracheal tube, a device for use in a medical procedure through a natural opening, and a medical procedure through a natural opening.

2. Description of the Related Art

Laparoscopy is known in which, instead of making a wide incision in the abdominal wall, a plurality of openings are formed in the abdominal wall and manual procedures are performed by inserting a rigid laparoscope, forceps, and a surgical knife, into the separate openings, in the case in which medical procedures (including observation, procedure, or the like; the same goes in the following) are performed on internal organs of a human body. Laparoscopy has an advantage in that early recovery of a patient can be expected since it requires only forming small openings in the abdomen.

However, in recent years, as for manual procedures which further reduce the burden on the patient, performing manual procedures by inserting a flexible endoscope through natural openings such as the mouth, the nose, or the anus, of the patient has been proposed. One example of such a medical procedure is disclosed in U.S. Pat. No. 5,458,131. This medical procedure will be explained. A flexible endoscope is inserted through the mouth of a patient; and the endoscope is fed into the abdominal cavity through an opening formed in the stomach wall. Observation of the abdominal cavity is performed by observation device provided on a distal end of the endoscope. Furthermore, procedure of an organ is performed by using: a treatment tool which passes through the endoscope; or a treatment tool which is inserted into the abdominal cavity through another opening formed in the stomach, or which is inserted from the anus into the abdominal cavity through an opening formed in the lower digestive tract. When the manual procedures within the abdominal cavity are completed, the treatment tool for an endoscope is removed; and the opening is closed. When closing the opening, the organs around the opening are drawn together and closed such that the organs are bound together by an O-ring.

SUMMARY OF THE INVENTION

An endotracheal tube according to a first aspect of the present invention is used by being installed into a patient so as to use it together with a device having an insertion section which is inserted into the body. A portion overlapping with the device inserted into the patient is formed as a flat shape; and furthermore, an outer face portion formed along a longitudinal direction of a cross-section, of the portion formed in the flat shape contacts the device.

A device for use in a medical procedure through a natural opening according to a second aspect of the present invention includes: an over-tube which guides an endoscope when the endoscope is inserted therein; and an endotracheal tube which is used by being installed into a patient through a mouth or through a nasal cavity, wherein an endotracheal-tube accommodating section having a non-circular shape and enabling surface-contact with the endotracheal tube is formed at a portion overlapping with the endotracheal tube of the over-tube, while the over-tube is installed into the patient.

A medical procedure through a natural opening according to a second aspect of the present invention includes: installing an endotracheal tube into a patient through a mouth or through a nasal cavity; inserting a device having an insertion section to be inserted into a body of the patient, into the body of the patient; and performing a desired procedure in the body of the patient using the device.

An endotracheal tube according to fourth aspect of the present invention has a distal end portion and a proximal end portion; is installed into a body of a patient through a mouth or through a nasal cavity; and includes a portion having a cross-sectional shape flatter than the distal end portion or at the proximal end portion, which is formed at a portion overlapping with a device having an insertion section to be inserted into the body when the endotracheal tube is installed into the patient and is used together with the device. A side face in a shorter-length direction of the cross-section, of the portion having a flat shape, contacts the device.

DETAILED DESCRIPTION OF THE INVENTION

A detailed explanation of embodiments will be made in the following. Moreover, in the following, the same symbols are applied to the same constituent elements. Furthermore, duplicated explanations will be omitted.

First Embodiment

Figure 1:
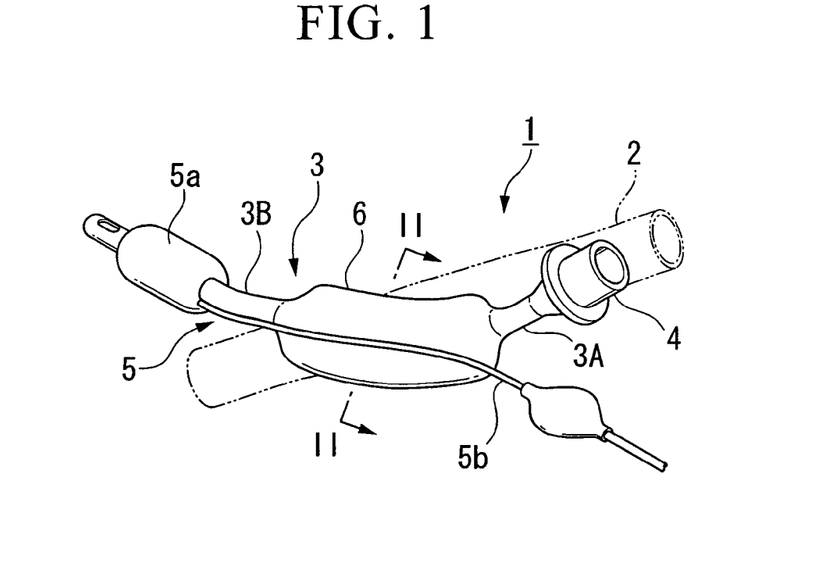
FIG. 1 shows a view showing an endotracheal tube of a first embodiment.

FIG. 1 shows an endotracheal tube of a first embodiment. This endotracheal tube is used by installing it into a patient through the mouth. In addition, the endotracheal tube 1 is used together with an over-tube 2 (one example of a device having an insertion section to be inserted into a body of the patient) which is used for guiding an endoscope through the mouth, and is used by being installed into the patient. Moreover, there is also a case in which this endotracheal tube 1 is used together with the endoscope (one example of another device) which is used through the mouth, instead of using the over-tube 2; and the endotracheal tube 1 is used by being installed into the patient.

The endotracheal tube 1 includes a tube main body 3; a connecting portion 4 which is attached to a proximal end of the tube main body 3, and is to be connected to a respirator; and an anchoring portion 5 which anchors the endotracheal tube 1 to a predetermined location in a body of a patient PT. The anchoring portion 5 includes a cuff balloon 5a, and a cuff tube 5b for supplying air into the cuff balloon 5a.

Figure 2:
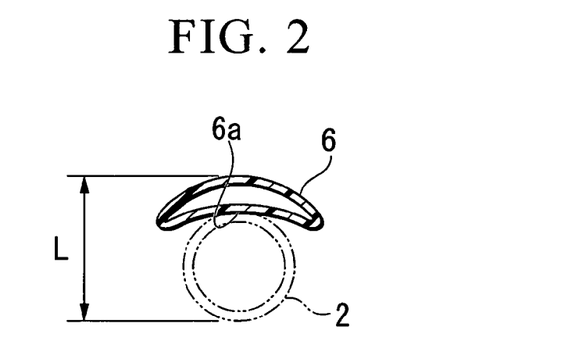
FIG. 2 shows a cross-sectional view taken along line II-II of FIG. 1.

The tube main body 3 is made from a material such as rubber, which is flexible and is harmless to the human body. Each of a proximal end 3A and a distal end 3B of the tube main body 3 has a circular cross-sectional shape. A flat portion 6 having a flat shape is formed in a middle portion of the tube main body 3. A cross-sectional face of the flat portion 6 explained herein is not limited to a crescent-shape as shown in FIG. 2, and may be of other cross-sectional shapes such as a rectangular shape, a semi-circular shape, an elliptical shape, or the like. That is, the flat portion 6 may be one having a cross-sectional face which is not a full-circular shape and of which the longer and shorter area axes can be specified.

A portion of the tube main body 3 where the flat portion 6 is formed, is a portion which is to overlap with the over-tube 2 for guiding the endoscope or with the endoscope to be inserted into the patient PT through the mouth, when the endotracheal tube 1 is installed into the patient PT through the mouth. That is, when viewed from the patient side, the portion of the tube main body 3 where the flat portion 6 is formed, is a portion to be located at a position from the larynx 7 to the musculus arytenoideus transversus 8. In specifically, the flat portion 6 is formed within a range approximately of 50 mm to 150 mm, from the distal end towards the proximal end side of the endotracheal tube 1.

When the endotracheal tube 1 is installed into the patient PT through the mouth and the endoscope or the over-tube 2 is further installed into the patient PT through the mouth, in a portion formed in a flat shape of the endotracheal tube 1 (i.e., the flat portion 6), an outer surface portion 6a of the flat portion 6, formed along the length in the cross-sectional face will contact the endoscope or the over-tube 2 as shown in FIG. 2.

A cross-sectional area of the flat portion 6 is set to be substantially equal to a cross-sectional area of a circular cross-sectional portion formed on the side of the proximal end portion or the distal end portion of the endotracheal tube 1. Furthermore, an external diameter (also an internal diameter) of the flat portion 6 is set to be smaller than an external diameter (an internal diameter) of the proximal end 3A or the distal end 3B.

Next, a procedure of the first embodiment will be explained. In the following, as one example of a medical procedure, an explanation will be given for a manual procedure in which the endoscope 1 (a device for performing medical procedures) is inserted through the mouth of the patient PT, and a desired procedure is performed in the abdominal cavity through an opening formed in the stomach wall. The medical procedure may be one of a variety of procedures such as suturing, observation, incision, inoculation of cells, extraction of internal organs, anastomosis between the lumen internal organs, and the like.

Firstly, the patient is anesthetized.

Figure 4:
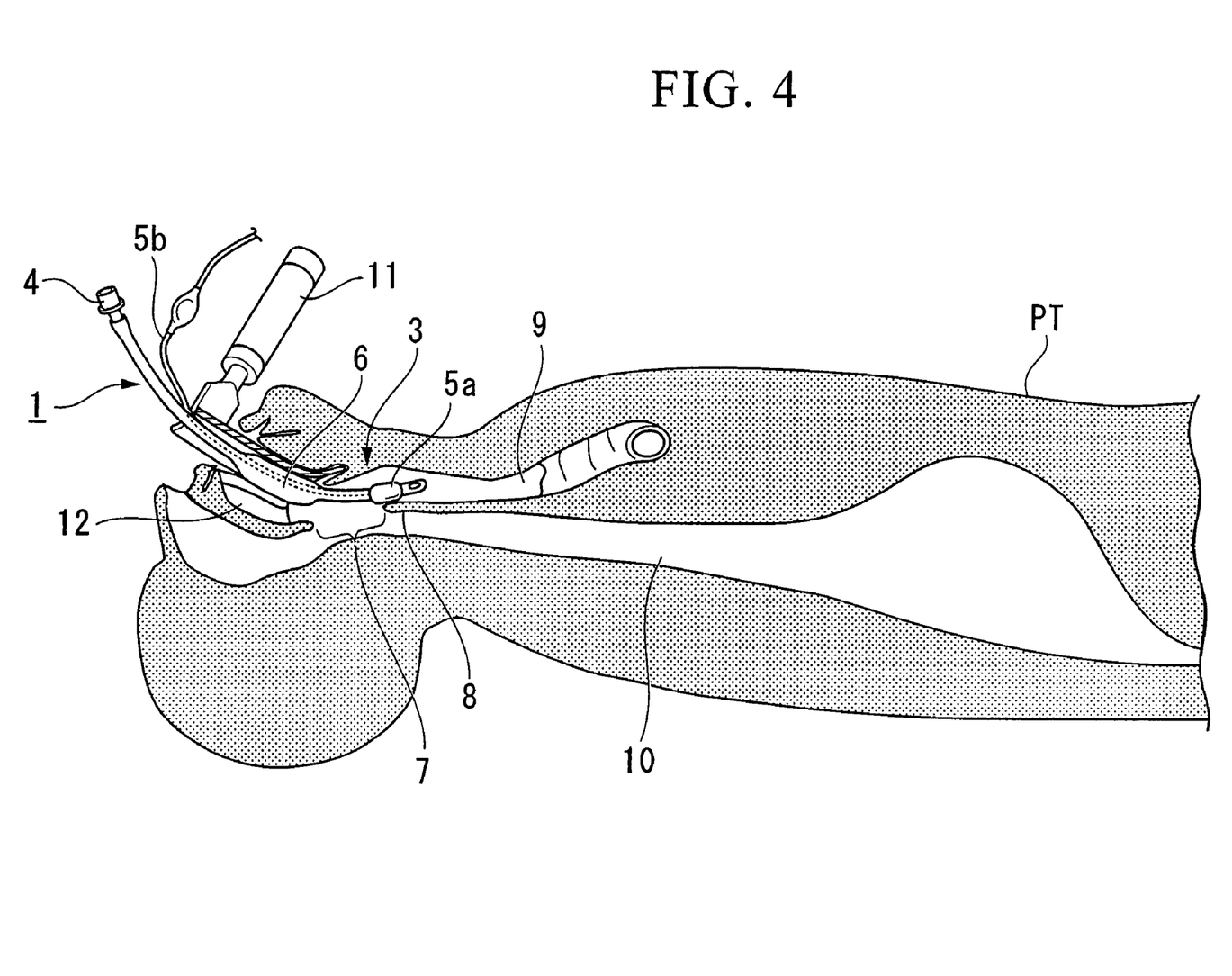
FIG. 4 shows an explanatory view of when the endotracheal tube is installed into a patient.

Next, as shown in FIG. 4, the head of the patient PT is directed downwards and is fixed such that each of the trachea 9 and an esophagus 10 becomes substantially straight. By this, a passage from the larynx 7 to the musculus arytenoideus transversus 8 of the patient PT can be made substantially linear; and furthermore, an interference portion between the over-tube 2 to be installed later and the endotracheal tube 1 can be shortened.

Next, as shown in FIG. 4, the endotracheal tube 1 is inserted through the oral cavity 12 of the patient PT using a laryngoscope 11. When the distal end of the endotracheal tube 1 reaches a predetermined length on the lung side from the cricoid cartilage, the endotracheal tube 1 is anchored by the anchoring member 5. That is, the endotracheal tube 1 is anchored by supplying air into the cuff balloons 5a through the cuff tube 5b and thereby expanding the cuff balloons 5a. At this time, the flat portion 6 of the endotracheal tube 1 is located within a region between the larynx 7 and the musculus arytenoideus transversus 8 of the patient PT. Next, the connecting portion 4 of the anchored endotracheal tube 1 is connected to the respirator; thereby, supplying necessary air, oxidant gas, or anesthesia gas into the lungs of the patient PT, and artificially controlling the breathing of the patient PT.

Figure 5:
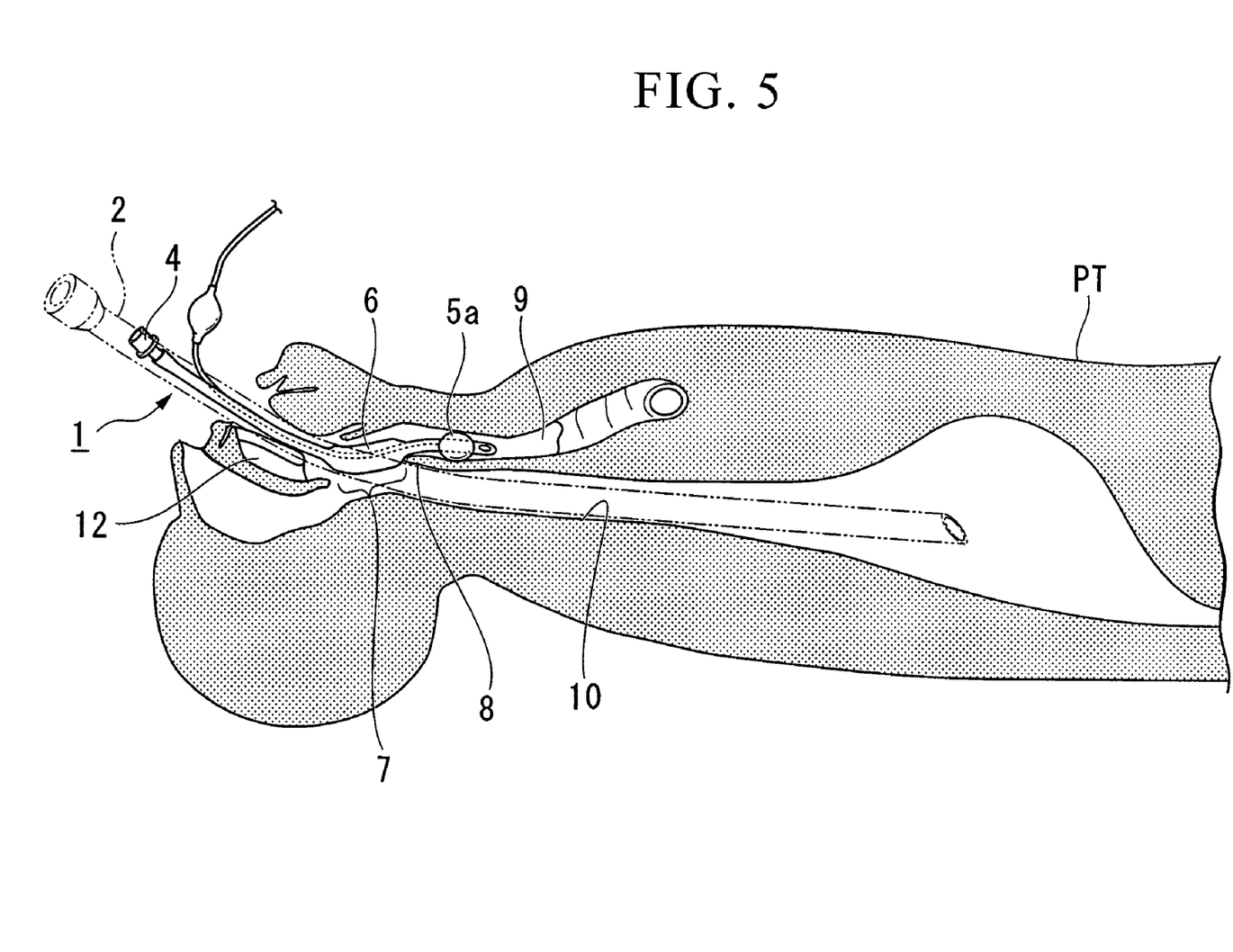
FIG. 5 shows an explanatory view of when the endotracheal tube is installed into a patient.

Next, as shown as a dotted line in FIG. 5, the distal end of the over-tube 2 (a device used for performing medical procedures the same as the endoscope) is inserted through the oral cavity 12 of the patient PT until the distal end thereof reaches the inside of the esophagus 10. At this time, the endoscope is used together, so as to be inserted into the body through the inside of the over-tube.

At this time, the endotracheal tube 1 anchored in advance and the over-tube 2 to be newly inserted will interfere within a region between the larynx 7 and the musculus arytenoideus transversus 8 of the patient PT; however, the endotracheal tube 1 is provided with the flat portion 6, and the outer surface 6a of the flat portion 6 along the length contacts the over-tube 2. In addition, the shorter diameter of the flat portion 6 is set to be smaller than the external diameter of the proximal end portion 3A or the distal end portion 3B. Therefore, as shown in FIG. 2, the width L of an overlapped portion between the flat portion 6 of the endotracheal tube 1 and the over-tube (or an inserting device such as an endoscope) can be comparatively smaller (i.e., the width of a portion overlapped with an inserting device can be smaller compared to the case in which a substantially circular-shaped endotracheal tube having no flat portion 6 is used). As a result, the burden on the larynx 7 of the patient PT can be decreased. At this time, since the cross-sectional area of the flat portion 6 is set to be substantially equal to that of a circular cross-sectional portion at the distal end portion or the proximal end portion of the endotracheal tube, there is no possibility of causing a problem in which the air-supply amount through the endotracheal tube is decreased by the formed flat portion 6.

Moreover, in the case in which a conventional endotracheal tube having a circular cross-sectional face from the proximal end to the distal end is used, the endotracheal tube and the over-tube, each having a circular-cross section, will be overlapped with each other within a range from the larynx 7 to the musculus arytenoideus transversus 8 of the patient PT (i.e., a portion where the digestive organ system and the respiratory organ system intersect each other); thereby, greatly increasing the width of the overlapped portion. Thus, the burden on the larynx of the patient greatly increases. When the distal end of the endoscope reaches the stomach, gas is supplied into the stomach using a channel in the endoscope; thereby expanding the stomach. Then, the stomach wall is incised by a high-frequency knife inserted in a channel within the endoscope.

Subsequently, an insufflate needle is embedded in the abdomen of the patient PT, and carbonic acid gas or the like is supplied into the abdominal cavity; thereby expanding the abdominal cavity. The reason for expanding the abdominal cavity is to secure space for performing medical procedures in the abdominal cavity. As for a method for expanding the abdominal cavity, carbonic acid gas may be supplied into the abdominal cavity using a channel within the endoscope instead of using the insufflate needle.

The diaphragm of the patient PT is pressed while in the insufflate condition. Especially, in the case in which the amount of anesthesia is large, natural breathing becomes hard; therefore, breathing of the patient is controlled by using the endotracheal tube 1.

Subsequently, an insertion portion of the endoscope is advanced into the abdominal cavity through an opening formed by the incision of the stomach wall, while replacing the over-tube 2 and the endoscope in accordance with necessity; and thereafter, the predetermined procedure is performed in the abdominal cavity using the endoscope.

Moreover, the reason for replacing the over-tube 2 in accordance with necessity is that the required cleanliness is different between the inside of the stomach and the inside of the abdominal cavity. Furthermore, the reason for replacing the endoscope is, the same as for the over-tube 2, that the required cleanliness is different between the inside of the stomach and the inside of the abdominal cavity; and the most suitable device for the procedure at that time needs to be used. However, in the case in which procedure can be easily performed using the same device, or in the case in which medical procedures are performed in the luminal internal organs without approaching the inside of the abdominal cavity, the devices such as the over-tube or the endoscope may not need to be replaced.

While replacing the over-tube 2 or the endoscope in this way, there has been a possibility of applying severe burden on the larynx, which is narrow, for the patient PT; however, also in this case, the burden on the patient PT can be decreased since, as mentioned above, the overlapping portion of the endotracheal tube 1 which overlaps with the over-tube 2 is made as the flat portion 6, thereby enabling a reduction in the width L of the overlapping portion between the endotracheal tube 1 and the over-tube.

Furthermore, since breathing control is performed using the endotracheal tube 1, it is also possible to switch from manual procedure using the endoscope to conventional manual procedure in which the abdominal wall is widely incised, during the procedure, in accordance with necessity.

When the necessary procedure inside the abdominal cavity is completed, the distal end of the endoscope is retracted to the inside of the stomach wall; and the opening portion is sutured by a treatment tool for suturing. A suture in the present invention is to close a communication between the inside of the lumen internal organs and the inside of the abdominal cavity; and closing a communication between the inside of the luminal internal organs and the inside of the abdominal cavity using a way such as anastomosis, is also included in the category of suturing.

Subsequently, the endoscope and the over-tube 2 are each removed from the patient PT; and furthermore the endotracheal tube 1 is removed from the patient PT when breathing control of the patient becomes unnecessary.

Figure 3:
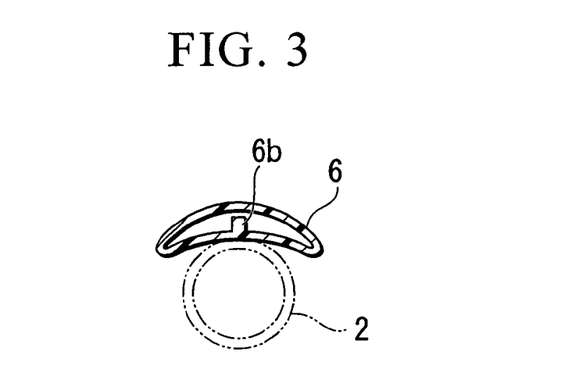
FIG. 3 shows a cross-sectional view of the endotracheal tube.

Moreover, in the first embodiment, the flat portion 6 is formed at a portion at which the endotracheal tube 1 and the over-tube overlap with each other in the larynx of the patient PT; however, as shown in FIG. 3, a reinforcing member such as a rib 6b which suppresses compression in the shorter direction of the flat portion 6 may be provided at substantially the middle portion along the length of an inner surface of the flat portion 6. In this case, collapsing of the flat portion 6 can be suppressed by the rib 6b even when the over-tube 2, the larynx, or the like applies an external force for compressing the endotracheal tube 1. Therefore, an internal space inside the flat portion 6 can be secured more reliably even when the endotracheal tube is made of a flexible material. Moreover, a plurality of ribs 6b may be provided. Furthermore, a rod-shaped member such as a wire for suppressing compression in the shorter axis of the flat portion may be provided as a reinforcing member so as to pass through at least the flat portion instead of the rib 6b.

Second Embodiment

Figure 6:
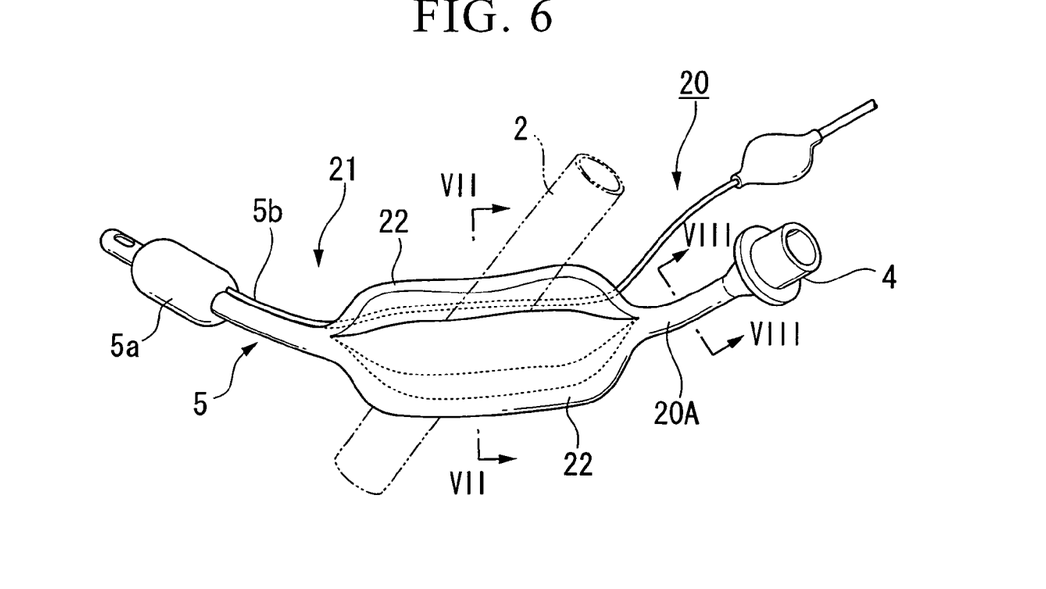
FIG. 6 shows a view showing an endotracheal tube of a second embodiment.
Figure 7:
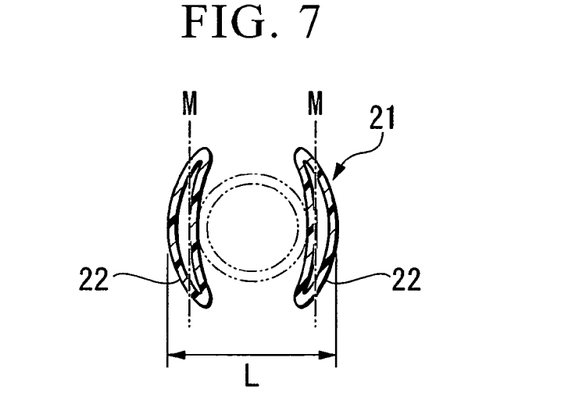
FIG. 7 shows a cross-sectional view taken along line VII-VII of FIG. 6.
Figure 8:
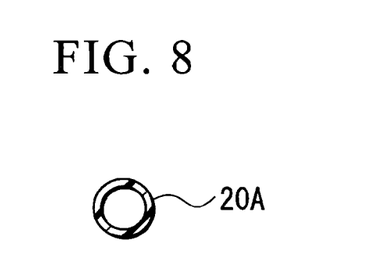
FIG. 8 shows a cross-sectional view taken along line VIII-VIII of FIG. 6.

FIG. 6 shows a second embodiment of an endotracheal tube. The same as the above-mentioned first embodiment, this endotracheal tube 20 is also used by being installed into a patient through the mouth. This endotracheal tube 20 has special features in that a portion of a tube main body 21, overlapping with the endoscope or the over-tube 2 to be inserted into the patient PT through the mouth when it is installed into the patient (i.e., an interfering portion) is formed into a plurality of (two in FIG. 7) branching passages 22; and the above-mentioned over-tube 2 passes between the branching passages 22. Each of these branching passages 22 is also formed in a flat shape. As shown in FIG. 7, the branching portions 22 formed in the flat shape are formed such that their longitudinal directions M in a cross section are parallel with each other.

In addition, a total cross-sectional area of the pluralities of branching passages 22 is set to be substantially equal to a cross-sectional area of a circular cross-sectional portion formed on the side of the proximal end portion 20A or the distal end portion of the endotracheal tube 20. The total width of the branching portions 22 in the shorter direction which are substantially orthogonal to the longitudinal directions M in a cross section set to be shorter than an external diameter of the endotracheal tube on the distal end side or the proximal end side.

In the case in which this endotracheal tube 20 is used, as shown in FIG. 7, the width L of an overlapping portion between the over-tube 2 and the branching portions 22 of the endotracheal tube 1 can be comparatively small; therefore, as a result, it becomes possible to reduce the burden on the larynx of the patient while securing the necessary amount of air supplied from the endotracheal tube 20. In addition, since a half way portion of a tube main body 21 is divided into a plurality of branching passages 22, compression of tissue around the larynx of the patient can be decreased when inserting the endoscope or the over-tube. At this point, the burden on the larynx of the patient can be further decreased.

Moreover, in FIG. 6 and FIG. 7, an explanation is given for an example in which two branching passages 22 are formed; however, there is no limitation to this, and the number of the branching passages 22 may be equal to or more than three. Furthermore, as same as the first embodiment, a reinforcing member for suppressing compression in the shorter axis of the branching passages 22 may be provided.

Third Embodiment

Figure 9:
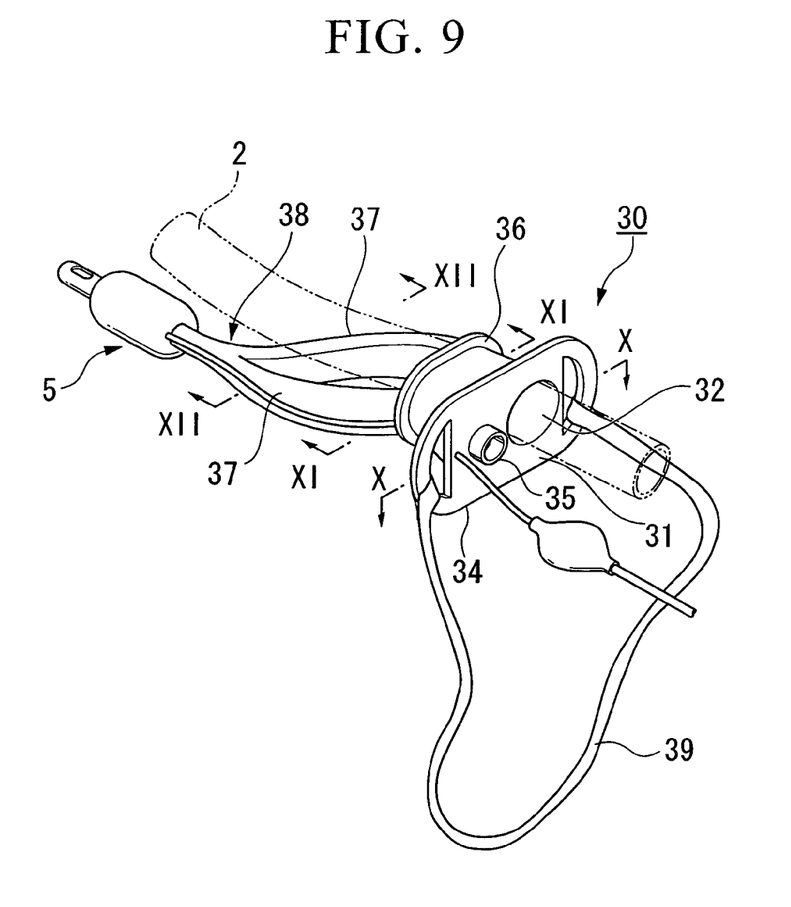
FIG. 9 shows a view showing an endotracheal tube of a third embodiment.
Figure 10:
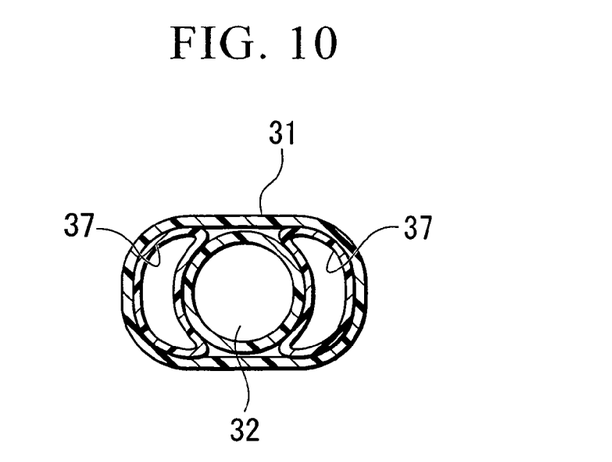
FIG. 10 shows a cross-sectional view taken along line X-X of FIG. 9.
Figure 11:
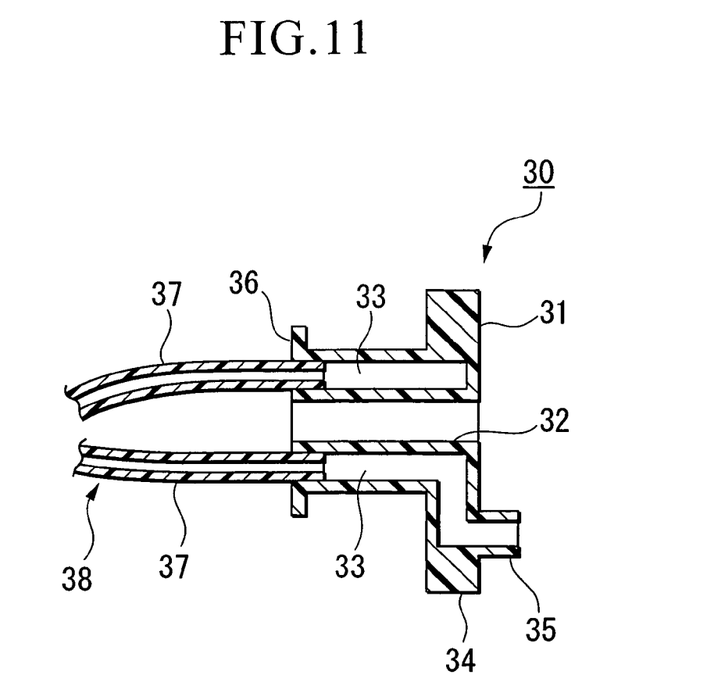
FIG. 11 shows a cross-sectional view taken along line XI-XI of FIG. 9.

FIG. 9 shows an endotracheal tube of a third embodiment. The same as the above-mentioned first embodiment, this endotracheal tube 30 is also used by being installed into a patient through the mouth. A special feature of this endotracheal tube 30 is that a mouthpiece 31 is attached to a proximal end side thereof. An insertion hole 32 for inserting the endoscope or the over-tube 2 is formed at the middle portion of the mouthpiece 31. A space 33 is formed on the outer side of the insertion hole 32 of the mouthpiece 31. The space 33 communicates with a connecting portion 35 provided on a frontal plate portion 34 of the mouthpiece 31; and branching passages 37 inserted into the bottom plate portion 36 of the mouthpiece 31. The total width of the branching portions 37 in the shorter direction which are substantially orthogonal to the longitudinal directions M in a cross section set to be shorter than an external diameter of the endotracheal tube on the distal end side or the proximal end side.

Figure 12:
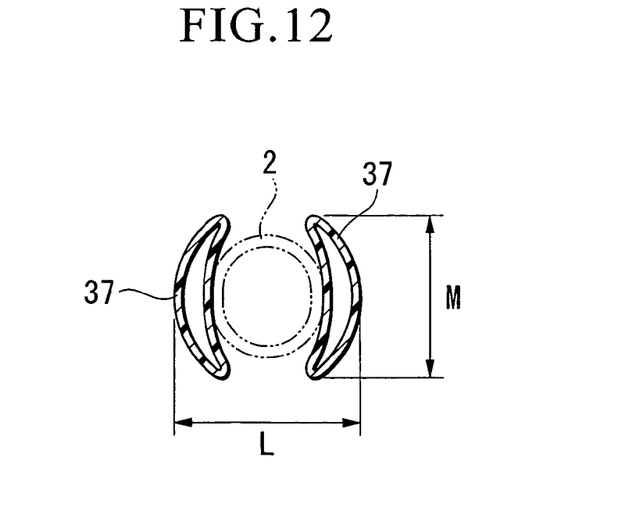
FIG. 12 shows a cross-sectional view taken along line XII-XII of FIG. 9.

Moreover, in FIG. 9, a reference symbol 39 denotes a string for fixing the mouthpiece 31 onto the mouth of the patient; and it is brought to the back of the head of the patient and is bound. In this endotracheal tube 30, branching passages 37 of a tube main body 38 are formed so as to be separated within a region where a tube main body 31 overlaps with the endoscope or the over-tube 2 to be inserted into the patient PT through the mouth when the endotracheal tube 30 is installed (i.e., an interfering portion). Also in this endotracheal tube 30, as shown in FIG. 12, the width L of an overlapping portion between the over-tube 2 and the branching portions 37 can be comparatively small; therefore, as a result, it becomes possible to reduce the burden on the larynx of the patient PT while securing the necessary amount of air-supply. Also in the present embodiment, the same as the first embodiment, a reinforcing member for suppressing compression in the shorter direction of the branching passages 37 may be provided.

Fourth Embodiment

Figure 13:
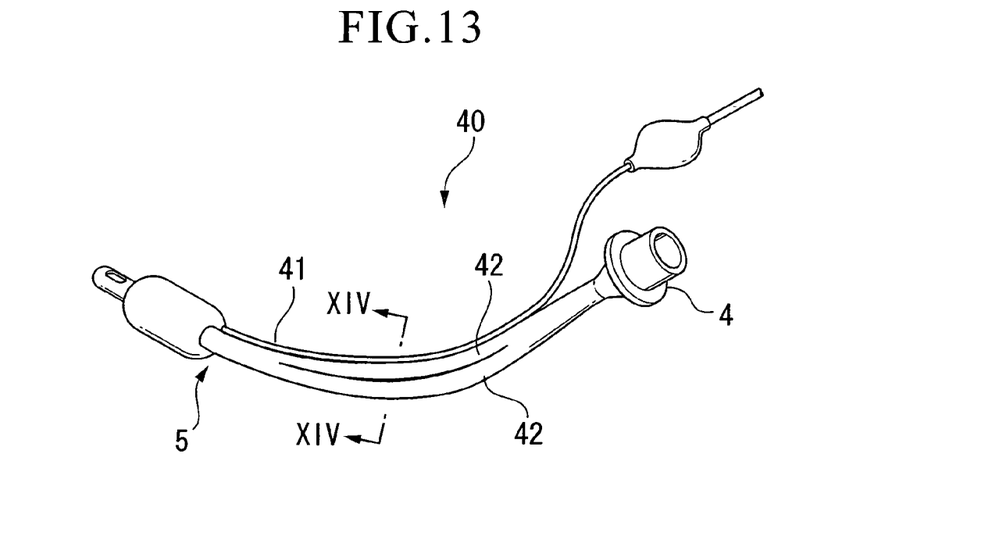
FIG. 13 shows a view showing an endotracheal tube of a fourth embodiment.

FIG. 13 shows an endotracheal tube of a fourth embodiment. This endotracheal tube 40 is also used by being installed into a patient through a nasal cavity. This endotracheal tube 40 has special features in that a portion overlapping with the endoscope or the over-tube 2 to be inserted into the patient through the mouth when it is installed into the patient (i.e., an interfering portion) is formed into a plurality of (two in FIG. 13) branching passages 42; and the branching passages 42 are formed in a semicircular cross-sectional shape of which flat portions 42a thereof face each other. The point that the endoscope or the over-tube 2 is inserted between these branching passages 22 is the same as in the second embodiment and the third embodiment. Also in the endotracheal tube 40, the total cross-sectional area of two branching passages 42 is set to be substantially equal to the cross-sectional area of a circular cross-sectional portion on the proximal end side or the distal end side.

The reason for forming the branching passages 42 into the semi-circular cross-sectional shape is to let them pass through the nose of the patient when installing the endotracheal tube 40 into the patient. That is, a passage of the nasopharynx is formed in a circular cross-sectional shape. In order to easily pass through this portion, the two branching passages 42 form a just circular cross-sectional shape when they are combined with each other.

Figure 14:
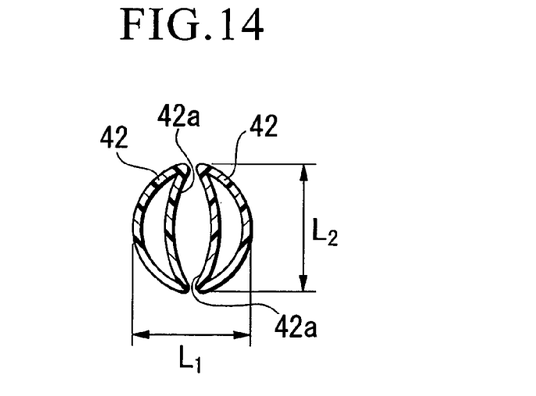
FIG. 14 shows a cross-sectional view taken along line XIV-XIV of FIG. 13.

More specifically, as shown in FIG. 14, a shape of each branching passage 42 is set such that a dimension L2 in the cross-sectional longitudinal direction when the two branching passages 42 are combined with each other is larger than a total dimension L1 in the cross-sectional shorter direction. Similarly, the reason for selecting a flat shape instead of a full-circular shape for the cross-sectional shape of the combined two branching passages 42, is in consideration of reducing the maximum external diameter of the portion overlapping with the over-tube 2 or the endoscope to be inserted into the patient through the mouth together with the branching passages 42. In the present embodiment, the insertionability through the nose is secured by setting the dimension L2 slightly larger than the dimension L1.

Figure 15:
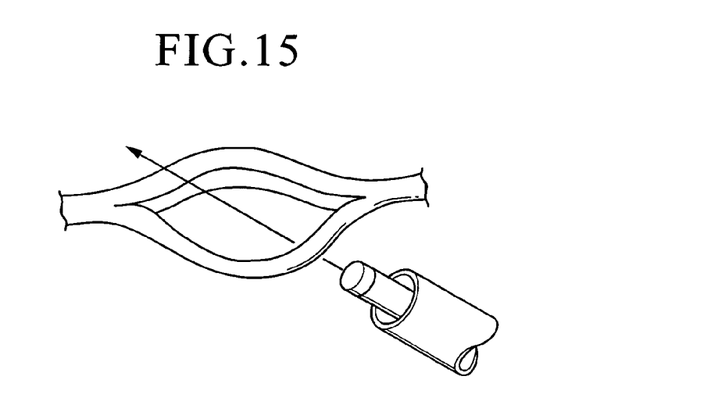
FIG. 15 shows an explanatory view of the endotracheal tube.
Figure 16:
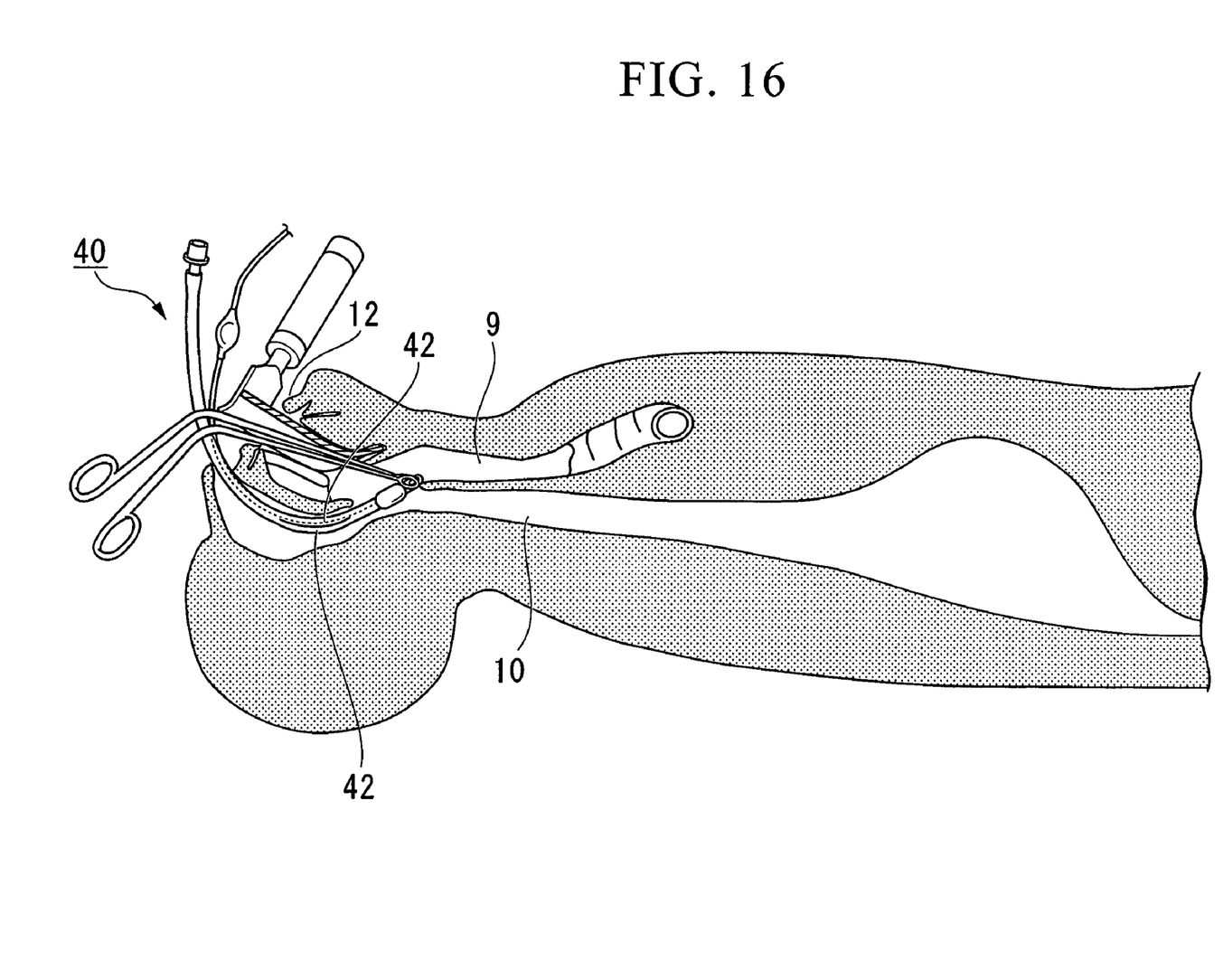
FIG. 16 shows an explanatory view when the endotracheal tube is installed into a patient.
Figure 17:
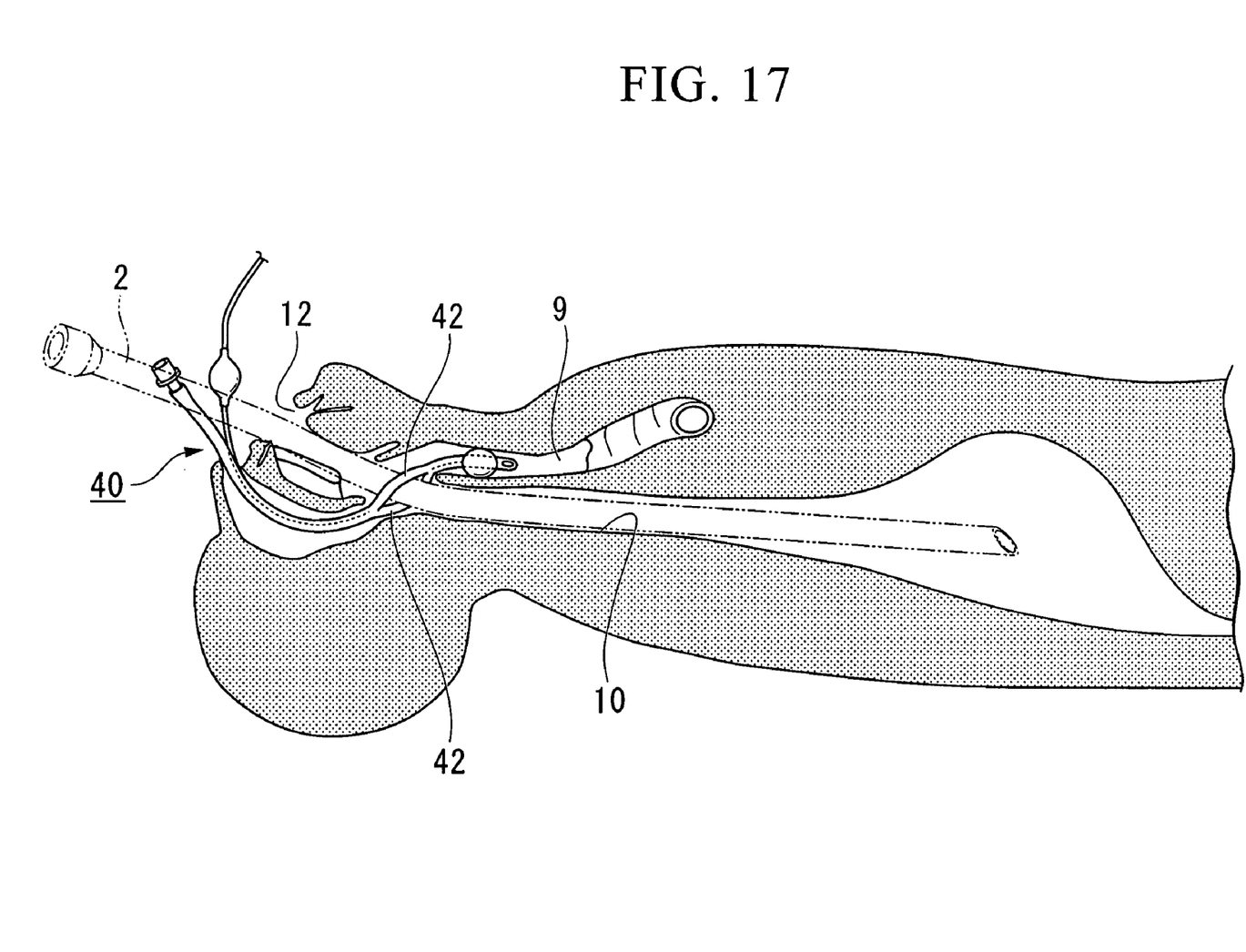
FIG. 17 shows an explanatory view when the endotracheal tube is installed into a patient.

FIG. 16 is for explaining the state in which the endotracheal tube 40 is installed into the patient PT through the nasal cavity. In order to guide the distal end of the endotracheal tube 40 into the trachea 9, forceps inserted through the oral cavity 12 may be used in accordance with necessity. Similarly, as shown by a dotted line in FIG. 17, for example, the over-tube 2 is inserted through the oral cavity of the patient PT after inserting the endotracheal tube 40 through the nose of the patient PT and anchoring it thereto. At this time, as shown in FIG. 15 and FIG. 17, it is inserted through an opening made between the two branching passages 42.

Moreover, it may be arranged such that the endotracheal tube 40 is made from a predetermined flexible material; and a state in which combining of the two branching passages 42 is secured by the elasticity thereof, while no external force is applied. In this case, insertion of the endoscope or the over-tube 2 through the two branching passages 42 can be done by opening these branching passages 42 using predetermined tools such as forceps.

Also in this endotracheal tube 40, the width of an overlapping portion between the branching passages 42 and the over-tube 2 can be comparatively small; therefore, as a result, it becomes possible to reduce the burden on the larynx of the patient PT while securing the necessary amount of air-supply.

Furthermore, according to the endotracheal tube 40, since it is installed through a nasal cavity, a length of a portion interfering with devices such as the endoscope or the over-tube can be shorter. That is, comparing to the case in which the endotracheal tube is inserted through the mouth, the burden on the patient can be further reduced since a length of the portion overlapping with devices such as the over-tube or the endoscope to be inserted through the mouth can be shorter. Furthermore, there is an advantage in that it is unlikely to be removed while inserting and removing the endoscope or the like since there is no interference in the oral cavity of the patient.

Fifth Embodiment

Figure 18:
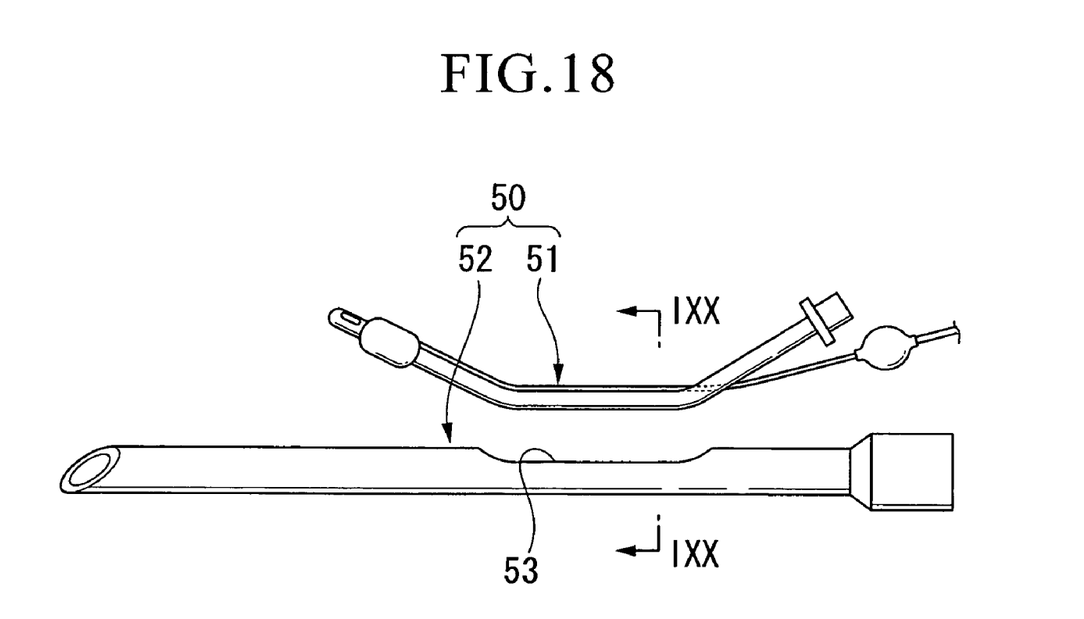
FIG. 18 shows an exploded view of an apparatus of a fifth embodiment which is to be used for medical procedure s through a natural opening.

FIG. 18 shows a tool used for medical procedures through the natural openings according to a fifth embodiment. This tool 50 is constituted by an endotracheal tube 51 and an over-tube 52. The endotracheal tube 51 is used by being installed into the patient through the mouth or through the nasal cavity. The over-tube 52 is used by being installed into the patient through the mouth.

An endotracheal-tube accommodating portion 53 having a non-circular-cross-sectional shape and capable of face-contacting with the endotracheal tube 51 is formed at a portion of the over-tube 52, overlapping with the endotracheal tube 51 installed into the patient while the over-tube 52 is installed into the patient. The endotracheal-tube accommodating portion 53 has, when it is seen in a cross-sectional view, a cross-sectional face in which one part of a circle is removed so as to be flattened.

Figure 21:
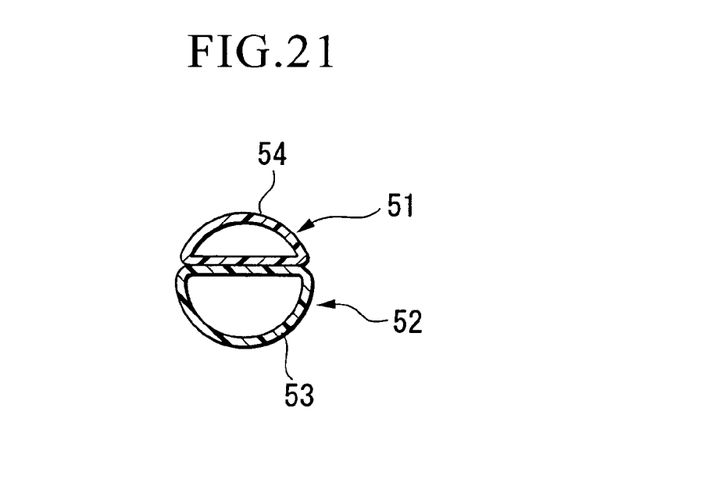
FIG. 21 shows a cross-sectional view taken along line XXI-XXI of FIG. 20.

A semi-circular cross-sectional portion 54 is formed at a position corresponding to the above-mentioned endotracheal-tube accommodating portion 53 of the endotracheal tube 51. The semi-circular cross-sectional portion 54 has a shape corresponding to a removed portion where the above-mentioned endotracheal-tube accommodating portion 53 is formed. That is, when a flat portion 53a of the endotracheal-tube accommodating portion 53 and a flat portion 54a of the semi-circular cross-sectional portion 54 overlap with each other, a circular cross-sectional shape is formed as shown in FIG. 21.

Also in the case in which the above-mentioned tool 50 for medical procedures through the natural openings is used, an overlapping portion between the endotracheal tube 51 and the over-tube 52 can be comparatively small (i.e., the width of the combined endotracheal-tube accommodating portion 53 and semi-circular cross-sectional portion 54 can be comparatively small); therefore, as a result, it becomes possible to reduce the burden on the larynx of the patient PT while securing the necessary amount of air-supply.

Figure 19:
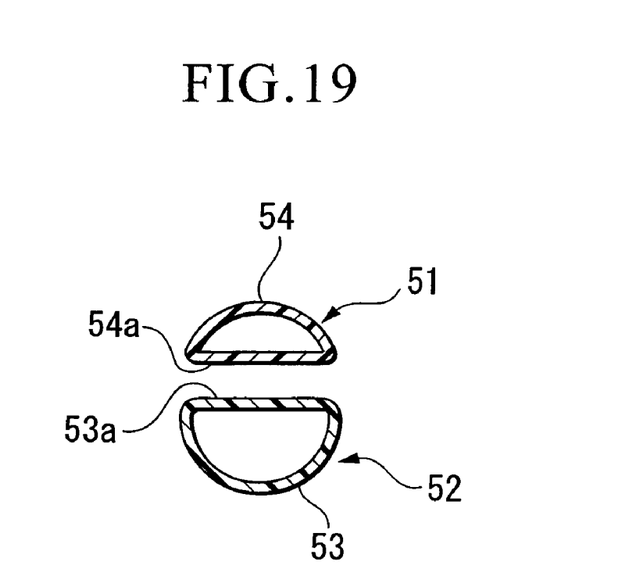
FIG. 19 shows a cross-sectional view taken along line IXX-IXX of FIG. 18.
Figure 20:
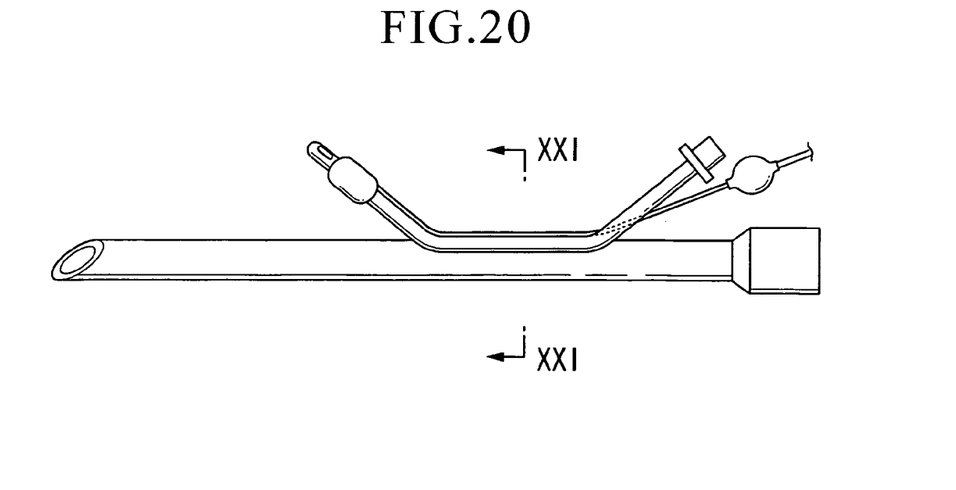
FIG. 20 shows an assembled status of the apparatus to be used for a medical procedure through a natural opening.
Figure 22:
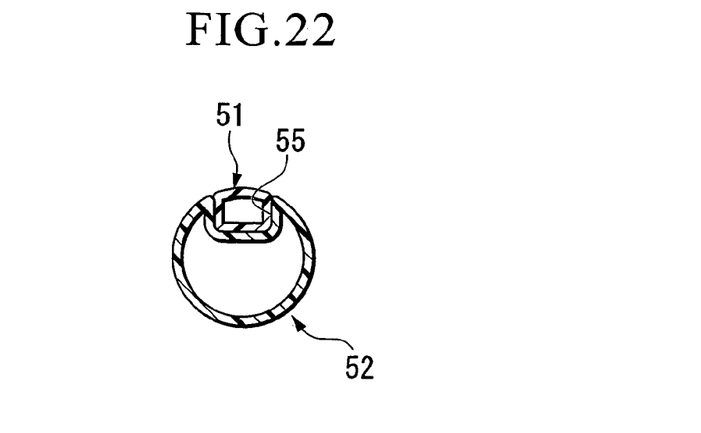
FIG. 22 shows a cross-sectional view of the apparatus to be used for medical procedures through a natural opening.

Moreover, combinations of the endotracheal tube 51 and the over-tube 52 are not limited to that disclosed in FIG. 18 and FIG. 19; and as shown in FIG. 22, the endotracheal-tube accommodating section 53 may be formed by a groove 55 which accommodates a part of the endotracheal tube 51. In addition, it may be arranged such that a cross-sectional shape of the over-tube has a different shape only at a portion interfering with the endotracheal tube. Furthermore, it may be arranged such that the entire range from a distal end to a proximal end of the insertion section of the over-tube has a different shape.

While preferred embodiments of the present invention have been explained in the above, it should be understood that the present invention is not limited to the above-mentioned embodiments. For example, for the embodiments, explanations are given for a manual procedure in which desired medical procedures are performed by introducing devices into the abdominal cavity through the opening; however, the hollow organ in which the opening is to be formed is not limited to the stomach, and it may be formed in any internal organs such as the esophagus or the duodenum, which can be approached through the mouth. Furthermore, manual procedure in which medical procedures are performed in the hollow organ without approaching the inside of the abdominal cavity may be included. Additions, omissions, substitutions, and other modifications can be made without departing from the spirit or scope of the present invention. The invention is not to be considered as being limited by the foregoing description, and is only limited by the scope of the appended claims.

What is claimed is:

1. An endotracheal tube which is used by being installed into a patient so as to use it together with a device having an insertion section which is for insertion into an upper digestive tract of the patient through a mouth, the endotracheal tube comprising:

an overlapping portion which overlaps with the device which is for installation into the patient having a flat shape; and an outer face portion formed along a longitudinal direction of a cross-section of the overlapping portion formed in the flat shape contacts the device, wherein the endotracheal tube slidably overlaps with the device at the overlapping portion thereof, and the overlapping portion includes a plurality of branching ducts each of which is formed in a flat shape.

2. The endotracheal tube according to claim 1, wherein a reinforcing member which suppresses compression in a shorter-length direction of the cross-section of the flat shape is, at least, provided at the overlapping portion formed in the flat shape.

3. The endotracheal tube according to claim 1, wherein:

the endotracheal tube is used by being installed into the patient through a mouth;

a mouthpiece is provided on a proximal end side;

an insertion hole for inserting the device is formed in the mouthpiece; and the branching ducts are each attached to left-and-right sides of the insertion hole so as to extend towards a distal-end side.

4. The endotracheal tube according to claim 1, wherein:

the endotracheal tube is used by being installed into the patient through a nasal cavity;

the overlapping portion includes two branching ducts each of which is formed in a flat shape; and each of the branching ducts is formed so as to have a semicircular cross-sectional shape in which flat portions thereof face each other.

5. The endotracheal tube according to claim 4, wherein:

the branching-ducts are made of a material having elasticity; and the flat portions contact each other due to the elasticity thereof, while an external force is not applied.

6. The endotracheal tube according to claim 1, wherein a cuff balloon is provided at a distal end thereof.

7. A device for use in a medical procedure through a natural opening, comprising:

an over-tube which guides an endoscope when the endoscope is inserted therein; and the endotracheal tube according to claim 1 which is used by being installed into a patient through a mouth or through a nasal cavity, wherein an endotracheal-tube accommodating section having a non-circular shape and enabling surface-contact with the endotracheal tube is formed at a portion overlapping with the endotracheal tube of the over-tube, while the over-tube is installed into the patient.

8. The device for use in a medical procedure through a natural opening, according to claim 7, wherein the endotracheal-tube accommodating section is formed by a groove portion which accommodates a part of the endotracheal tube.

9. The device for use in a medical procedure through a natural opening, according to claim 7, wherein when the endotracheal tube is accommodated into the endotracheal-tube accommodating section of the over-tube, an external shape of the both tubes, in which the over-tube and the endotracheal tube are overlapped with each other, is formed in a circular cross-sectional shape.

10. A medical procedure through a natural opening, comprising:

installing the endotracheal tube according to claim 1 into a patient through a mouth or through a nasal cavity;

inserting an insertion section of a device into the upper digestive tract of the patient; and performing a desired procedure in the body of the patient using the device.

11. The medical procedure through a natural opening, according to claim 10, wherein the performing of the desired procedure in the body of the patient includes: forming an opening in a wall of a hollow organ; approaching an abdominal cavity through the opening; and performing a desired medical procedure in the abdominal cavity.

12. The medical procedure through a natural opening, according to claim 11, further comprising closing a communication between an inside of the hollow organ and an inside of the abdominal cavity through the opening, after performing the desired medical procedure in the abdominal cavity.

13. An endotracheal tube which has a distal end portion and a proximal end portion; is adapted to be installed into a body of a patient through a mouth or through a nasal cavity; and comprises a portion having a cross-sectional shape flatter than that at the distal end portion or at the proximal end portion, which is formed at a portion overlapping with a device having an insertion section to be inserted into an upper digestive tract of the patient, when the endotracheal tube is installed into the patient and is used together with the device, wherein a side face in a longer-length direction of the cross-section of the portion having a flat shape, contacts the device, and the overlapping portion includes a plurality of branching ducts each of which is formed in a flat shape.

* * * * *